United States Patent
Kim et al.

(10) Patent No.: US 7,547,279 B2
(45) Date of Patent: Jun. 16, 2009

(54) SYSTEM AND METHOD FOR RECOGNIZING USER'S EMOTIONAL STATE USING SHORT-TIME MONITORING OF PHYSIOLOGICAL SIGNALS

(75) Inventors: Kyung-hwan Kim, Kyungki-do (KR); Seok-won Bang, Seoul (KR); Dong-geon Kong, Busan (KR)

(73) Assignee: Samsung Electronics Co., Ltd., Suwon, Kyungki-Do (KR)

( * ) Notice: Subject to any disclaimer, the term of this patent is extended or adjusted under 35 U.S.C. 154(b) by 1140 days.

(21) Appl. No.: 10/348,976

(22) Filed: Jan. 23, 2003

(65) Prior Publication Data

US 2003/0139654 A1    Jul. 24, 2003

(30) Foreign Application Priority Data

Jan. 23, 2002    (KR)    ................. 2002-3868

(51) Int. Cl.
    *A61B 5/00*    (2006.01)
(52) U.S. Cl. ............... 600/300; 600/301; 128/920
(58) Field of Classification Search ......... 600/300–301, 600/500–511, 517; 128/903–905, 925
    See application file for complete search history.

(56) References Cited

U.S. PATENT DOCUMENTS 5,365,934 A * 11/1994 Leon et al. .................. 600/517
5,375,604 A * 12/1994 Kelly et al. ................. 600/484
5,524,631 A *  6/1996 Zahorian et al. ............ 600/511
5,595,183 A *  1/1997 Swanson et al. ............ 600/510
5,676,138 A    10/1997 Zawilinski
6,599,243 B2 * 7/2003 Woltermann et al. ........ 600/300

FOREIGN PATENT DOCUMENTS

JP        04-314431        11/1992

(Continued)

OTHER PUBLICATIONS

Healey, Jennifer A., Wearable and Automotive Systems for Affect Recognition from Physiology, Jun. 22, 2000, Massachusetts Institute of Technology, Department of Electrical Engineering and Computer Science: Doctoral Thesis.*

(Continued)

*Primary Examiner*—Max F. Hindenburg
*Assistant Examiner*—Michael C. Astorino
(74) *Attorney, Agent, or Firm*—Buchanan Ingersoll & Rooney PC

(57) ABSTRACT

Disclosed is an emotion recognition apparatus and method thereof which enables perception of a user's emotional state by monitoring one or more of his or her physiological signals. The emotion recognition apparatus comprises a feature analyzer adapted to analyze features of the physiological signals acquired from a user and generate feature values, a subtractor adapted to obtain differences between the feature values generated by the feature analyzer and feature values used as a standard to perceive an emotional state of the user, and an emotion classifier adapted to analyze the differences obtained by the subtractor and classify an emotion into a plurality of emotional categories so as to perceive an emotional category exhibiting the greatest intensity to be the emotional state of the user.

14 Claims, 13 Drawing Sheets

FOREIGN PATENT DOCUMENTS

| | | |
|---|---|---|
| JP | 08-2348053 | 9/1996 |
| JP | 09-220208 | 8/1997 |
| JP | 09-238908 | 9/1997 |
| JP | 7-501154 | 2/1998 |
| JP | 11-511036 | 9/1999 |
| JP | 2001-112725 | 4/2001 |
| JP | 2001-190616 | 7/2001 |
| JP | 2001-204714 | 7/2001 |
| JP | 2001-246580 | 9/2001 |
| JP | 2001-299702 | 10/2001 |
| WO | WO 93/02622 | 2/1993 |
| WO | WO 96/08992 | 3/1996 |

OTHER PUBLICATIONS

Clark, Jr., John W., et al., Medical Instrumentation Application and Design Second Edition Houghton Mifflin Company, Boston, U.S.A. pp. 78-83 and 450-453.

Mukhopadhyay, Sudipta et al., "*a New Interpretation of Nonlinear Energy Operator and Its Efficacy in Spike Detection*," IEEE Transactions on Biomedical Engineering 45(2) pp. 180-187 (1998).

Berger, Ronald D., "*An Efficient Algorithm for Spectral Analysis of Heart Rate Variability*" IEEE Transactions on Biomedical Engineering 33(9) pp. 900-904 (1986).

Broersen, P.M.T., "*Facts and Fiction in Spectral Analysis*," IEEE Transactions on Instrumentation and Measurement 49(4) pp. 766-772 (2000).

Vapnik, Vladimir N., "*An Overview of Statistical Learning Theory*," IEEE Transactions on Neural Networks 10(5) pp. 988-999 (1999).

Clark, Jr., John W. et al., Medical Instrumentation Application and Design Second Edition Houghton Mifflin Company, Boston, U.S.A. pp. 78-83 and 450-453.

\* cited by examiner

SYSTEM AND METHOD FOR RECOGNIZING USER'S EMOTIONAL STATE USING SHORT-TIME MONITORING OF PHYSIOLOGICAL SIGNALS

BACKGROUND OF THE INVENTION

This application claims the priority of Korean Patent Application No. 2002-3868, filed on Jan. 23, 2002, which is incorporated herein in its entirety by reference.

1. Field of the Invention

The present invention relates to an emotion recognition system and method thereof, and more particularly, to an emotion recognition system and method thereof which enables perception of a user's emotional state by monitoring his or her physiological signals.

2. Description of the Related Art

An emotion refers to a mental state which is associated with certain physiological activity and is caused by internal or external environmental stimulus. Emotional states are broadly classified into positive emotions and negative emotions. The former includes happiness, contentment (pleasure), tranquility, elation, etc., and the latter includes sadness, discontent (displeasure), anger, surprise, fear, depression, etc. Besides these emotions, more diverse classification of emotions is possible. Herein, an example of internal stimulus includes an old memory or a subjective emotional stimulus, and an example of external stimulus includes stress or the relief of stress due to various environmental factors except for voluntary stimulus of an emotional subject.

Theories for defining emotions include the James-Lange theory in which an appropriate emotion is experienced by recognizing physiological changes of an autonomic nervous system upon the input of an external environmental stimulus to a human body, and the Cannon-Bard theory in which a physiological reaction to an external environmental stimulus and a psychological or emotional experience occur simultaneously. The difference between these two theories is that the former is based on a peripheral organ in the human nervous system being the origin of occurrence of an emotion, while the latter is based on the human brain being the origin of occurrence of an emotion.

As mentioned above, a change of an emotional state due to an internal or external environmental stimulus involves a change of physiological characteristics of a human body caused by an adjustment of an autonomic nervous system. Accordingly, a change of an emotional state can be recognized by measuring physiological signals reflecting physiological changes such as changes in heart beat, Electromyogram (EMG), electrodemal conductivity, body temperature, etc. An appropriate physiological signal sensor can measure these physiological signals.

Methods of recognizing an emotion based on a physiological signal acquired through a physiological signal sensor have already been disclosed in several associated patents. For example, a device for analyzing an emotional state caused by a stimulus from an external environmental stimulus means such as TV, etc., is disclosed in U.S. Pat. No. 5,676,138 to Zawilinski, issued October 1997 and entitled "EMOTIONAL RESPONSE ANALYZER SYSTEM WITH MULTIMEDIA DISPLAY". However, a problem with this method is that it shows only a limited amount of experimental data and a result, and an emotional state is identified through the use of a z-score, thereby resulting in a decreased accuracy of the emotional response analyzer.

SUMMARY OF THE INVENTION

To solve the above-described problems, it is an object of the present invention to provide an emotion recognition system and method thereof in which non-invasive physiological signals are acquired from a sensor like a wrist watch that can be worn on the body of a user, and a user's emotional state can be perceived on the basis of the non-invasive physiological signals.

It is another object of the present invention to provide an emotion recognition system and method thereof which more correctly perceives a user's emotional state by monitoring a physiological signal acquired from a user for a short time period.

In order to accomplish the above objects, there is provided an emotional recognizing system comprising a physiological signal acquiring unit adapted to acquire at least one physiological signal and wirelessly transmit the acquired physiological signal, the physiological signal acquiring unit being worn on the body of a user and an emotion recognition unit adapted to receive the physiological signal transmitted from the physiological signal acquiring unit and monitor it for a short time period to perceive an emotional state of the user.

According to another aspect of the present invention, there is also provided an emotion recognition apparatus, comprising a feature analyzer adapted to analyze features of physiological signals acquired from a user and generate feature values corresponding to the results of analysis, a subtractor adapted to obtain differences between the feature values of the analyzed results generated from the feature analyzer and feature values used as a standard to perceive an emotional state of the user, and an emotion classifier adapted to analyze the differences obtained by the subtractor to classify an emotion into a plurality of emotional categories and perceive an emotional category exhibiting the greatest intensity to be the emotional state of the user.

According to another aspect of the present invention, there is also provided an emotion recognition method, comprising the steps of receiving one or more physiological signals from a user, analyzing the received physiological signals and extracting a plurality of feature values to be used for recognition of an emotional state of the user in response to the result of analyzing the received physiological signals, calculating differences between the extracted plurality of feature values and predetermined feature values used as a standard to perceive an emotional state of the user, classifying an emotional state of the user into a plurality of emotional categories in response to the calculated differences, and selecting an emotion exhibiting the greatest intensity among the classified emotional categories as a resultant emotional state of the user and outputting the selected emotion.

BRIEF DESCRIPTION OF THE DRAWINGS

The above objects and advantages of the present invention will become more apparent by describing in detail preferred embodiments thereof with reference to the attached drawings in which.

DETAILED DESCRIPTION OF THE INVENTION

Hereinafter, preferred embodiments of the present invention will be described in detail with reference to the accompanying drawings.

Figure 1:
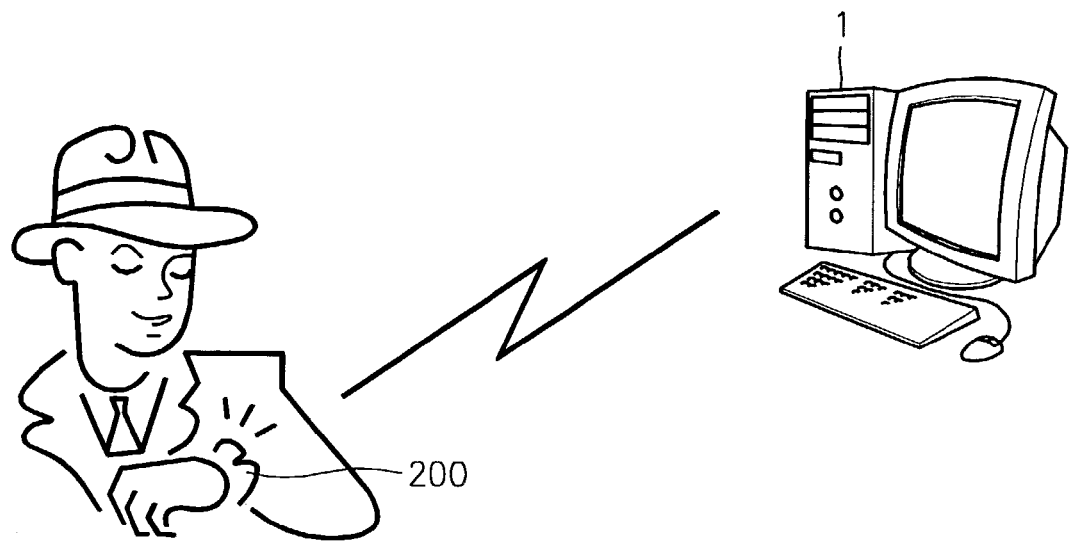
FIG. 1 is a schematic pictorial view illustrating the overall construction of an emotion recognition system according to a preferred embodiment of the present invention.
Figure 2A:
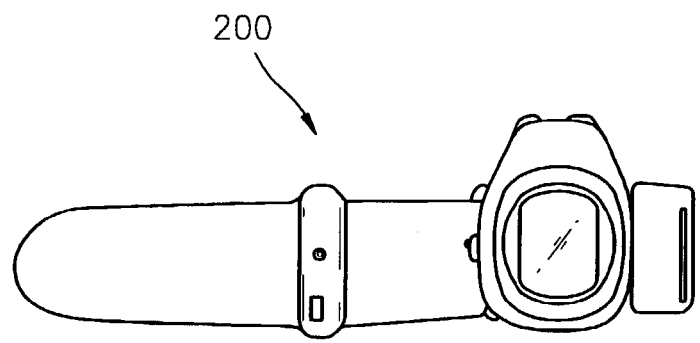
FIGS. 2A and 2B are schematic views illustrating the appearance of a physiological signal acquiring unit shown in FIG. 1.
Figure 2B:
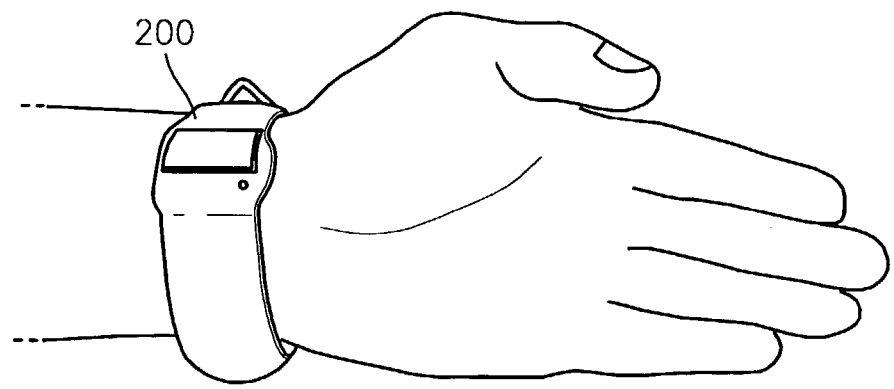

FIG. 1 is a schematic pictorial view illustrating the overall construction of an emotion recognition system according to a preferred embodiment of the present invention, and FIGS. 2A and 2B are schematic views illustrating the appearance of a physiological signal acquiring unit 200 shown in FIG. 1.

Referring to FIG. 1, there is shown an emotion recognition system including a physiological signal acquiring unit 200 and an emotion recognition unit 1.

As shown in FIGS. 1 and 2, the physiological signal acquiring unit 200 is worn on the body of a user in the form of a wrist watch for non-invasively measuring physiological signals of photoplethysmogram (hereinafter, referred to as "PPG"), electrocardiogram (hereinafter, referred to as "ECG"), electrodermal activity (hereinafter, referred to as "EDA"), skin temperature (hereinafter, referred to as "SKT"), etc. A physiological signal acquired through the physiological signal acquiring unit 200 is wirelessly transmitted to the emotion recognition unit 1 and is used to recognize a user's emotional state. The emotion recognition unit 1 is configured with a computer having an algorithm stored therein for analyzing the physiological signal input thereto from the physiological signal acquiring unit 200, or an arithmetic and logic unit (ALU) corresponding to the computer. The details of a sensor used to acquire the physiological signal are described in detail in "Medical Instrumentation" by J. G. Webster, 1999.

Figure 3:
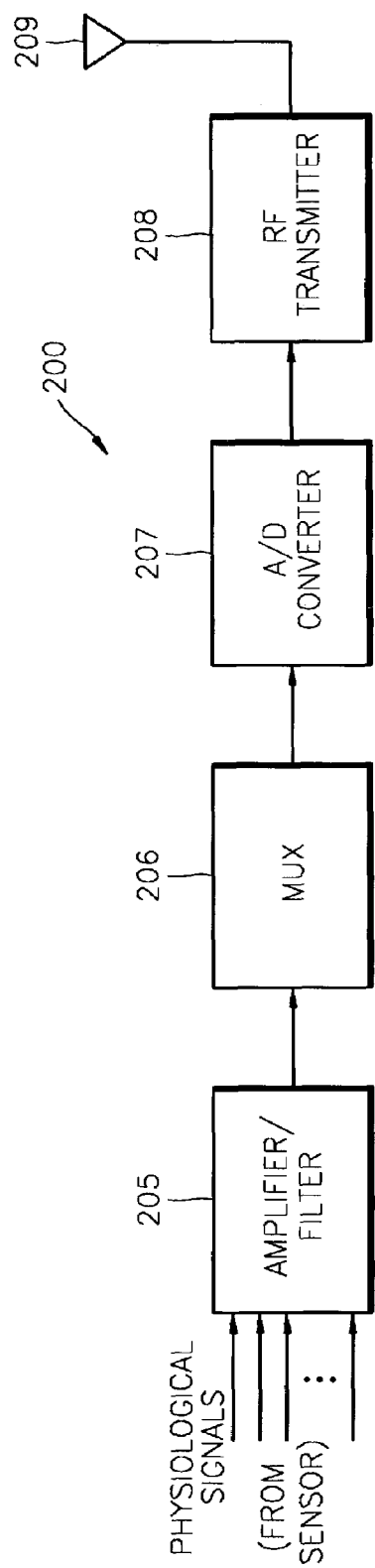
FIG. 3 is a block diagram illustrating the construction of the physiological signal acquiring unit of the emotion recognition system shown in FIG. 1.
Figure 4:
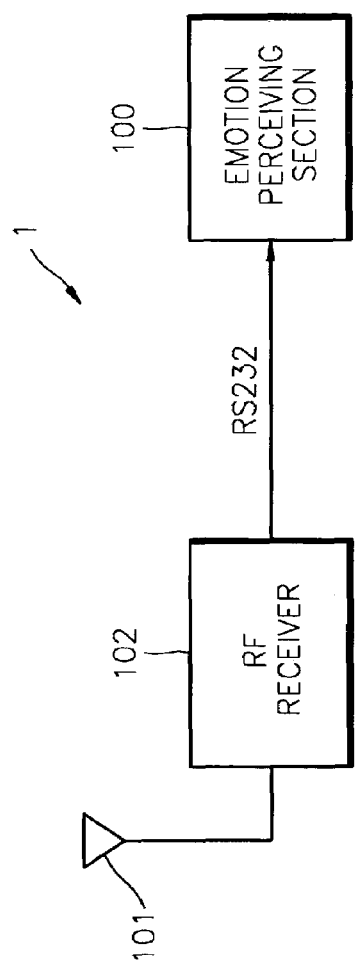
FIG. 4 is a block diagram illustrating the construction of an emotion recognition unit of the emotion recognition system shown in FIG. 1.

FIGS. 3 and 4 are block diagrams illustrating the construction of a physiological signal acquiring unit 200 and an emotion recognition unit 1 shown in FIG. 1.

Referring to FIG. 3, the physiological signal acquiring unit 200 includes one or more sensors for non-invasively sensing one or more physiological signals of a user, an amplifier/filter 205 for amplifying and filtering the one or more physiological signals applied thereto from the sensors, a multiplexer 206 for classifying each of the amplified and filtered physiological signals applied thereto from the amplifier-filter 205 and outputting the classified physiological signals, an analog-to-digital (A/D) converter 207 for converting the classified physiological signals applied thereto from the multiplexer 206 into the form of digital signals to output the converted digital signals, and a radio frequency (RF) transmitter 208 for converting the converted digital signals applied thereto from the A/D converter 207 into RF signals to wirelessly transmit the converted RF signals to the emotion recognition unit 1 through an antenna 209.

Referring to FIG. 4, the emotion recognition unit 1 includes an RF receiver 102 for receiving the physiological signals of the user transmitted from the physiological signal acquiring unit 200 through an antenna 101, and an emotion perceiving section 100 for analyzing the physiological signals received by the RF receiver 102 to perceive an emotional state of the user. Herein, transmission and reception of the physiological signals between the RF receiver 102 and the emotion recognition section 100 is carried out by a communication protocol such as RS232C. However, this is only an example of a signal transmission method, and diverse communication protocols may be employed depending on the configurations of circuits.

Figure 5:
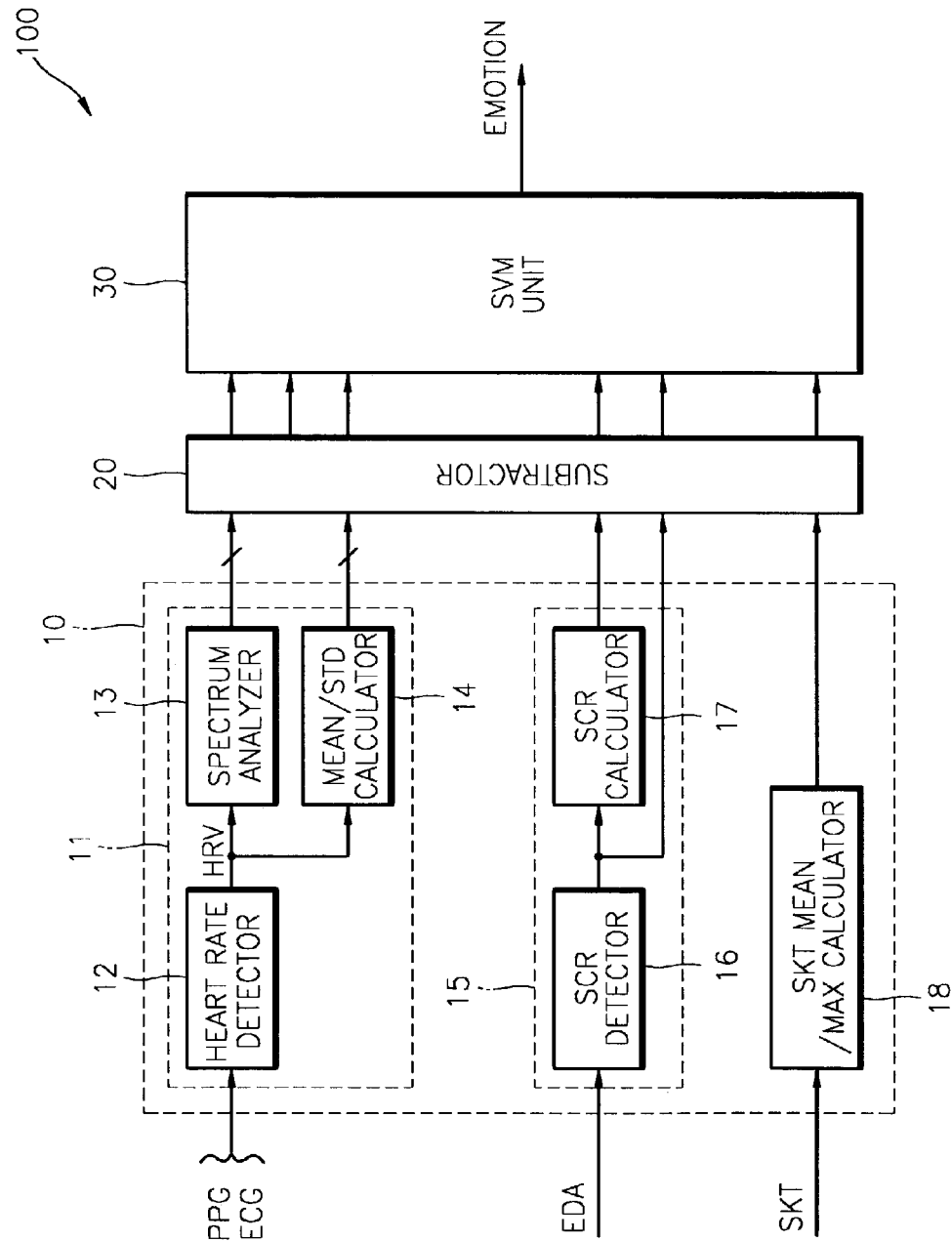
FIG. 5 is a block diagram illustrating the construction of an emotion perceiving section of the emotion recognition unit shown in FIG. 4.

FIG. 5 is a block diagram illustrating the detailed construction of an emotion perceiving section 100 of the emotion recognition unit shown in FIG. 4.

Referring to FIG. 5, the emotion perceiving section 100 is shown to include a feature analyzer 10 for analyzing features of the physiological signals acquired from the physiological signal acquiring unit 200, a subtractor 20 for obtaining differences between the results of analyzing the features generated from the feature analyzer 10 and feature values representing an ordinary emotional state of the user, a support vector machine unit (hereinafter, referred to as "SVM") 30 for analyzing difference values obtained by the subtractor 20 to classify emotions so as to perceive an emotional state of the user.

The feature analyzer 10 includes a heart rate analyzer 11 for receiving an ECG or PPG signal from the RF receiver 102 to detect a heart beat signal and extract the feature values associated with the detected heart beat signal which are supplied to the subtractor 20, a skin conductance response (hereinafter, referred to as "SCR") analyzer 15 for receiving an EDA signal from the RF receiver 102 to extract the feature values associated with SCR which are supplied to the subtractor 20, and an SKT Mean/Max calculator 18 for receiving an SKT signal from the RF receiver 102 to extract the feature values (i.e., a mean value (Mean) and a maximum value (Max) of SKT) associated with SKT which are supplied to the subtractor 20.

The heart rate analyzer 11 includes a heart rate detector 12 for receiving the ECG or PPG signal from the RF receiver 102 to detect the heart beat signal, a heart rate variability (HRV) extractor for extracting time series of heart rate variability (HRV) from the detected heart beat signal, a spectrum analyzer 13 for analyzing a spectrum of the extracted time series of the HRV, and a Mean/Std calculator 14 for calculating a Mean and a standard deviation value (Std) of the detected heart beat signal. Also, the SCR analyzer 15 includes an SCR detector 16 for receiving the EDA signal to detect SCR and an SCR calculator 17 for calculating parameters such as an amplitude of SCR.

Figure 6A:
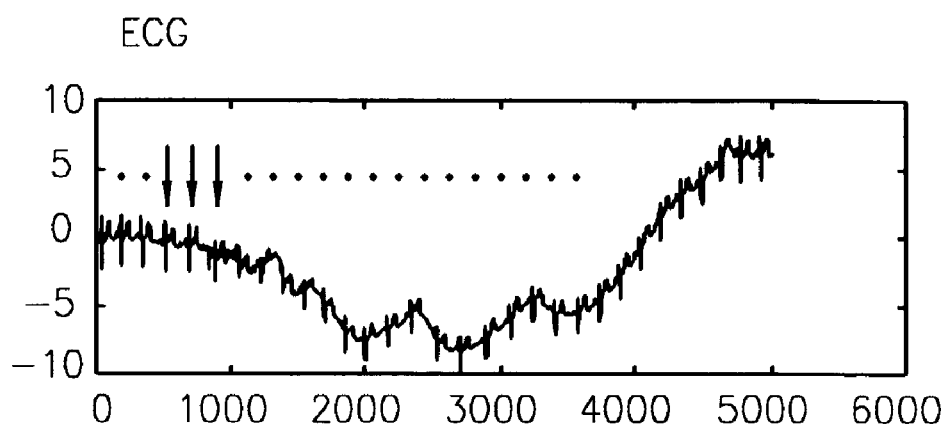
FIGS. 6A and 6B are graphs illustrating an example of electocardiogram (ECG) and photoplethysmogram (PPG) signals used in the analysis of a heart beat signal according to a preferred embodiment of the present invention.
Figure 6B:
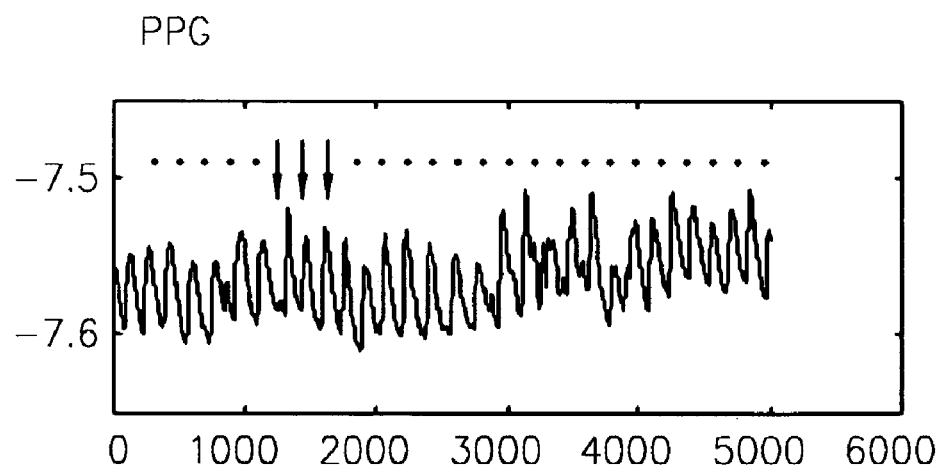
Figure 7:
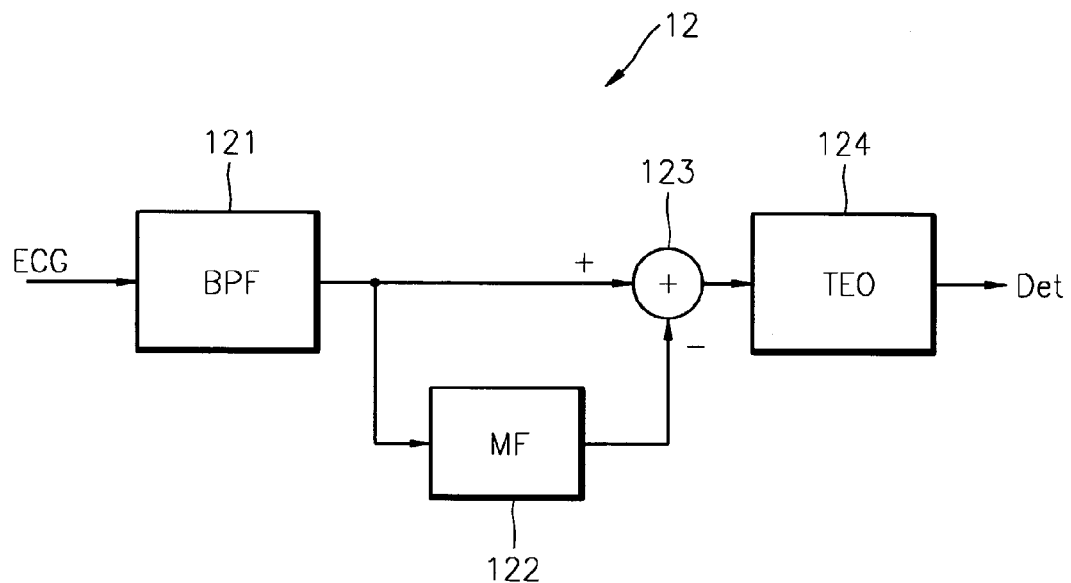
FIGS. 7 and 8 are block diagrams illustrating a detailed alternative construction of a heart beat detector of the emotion perceiving section shown in FIG. 5.
Figure 8:
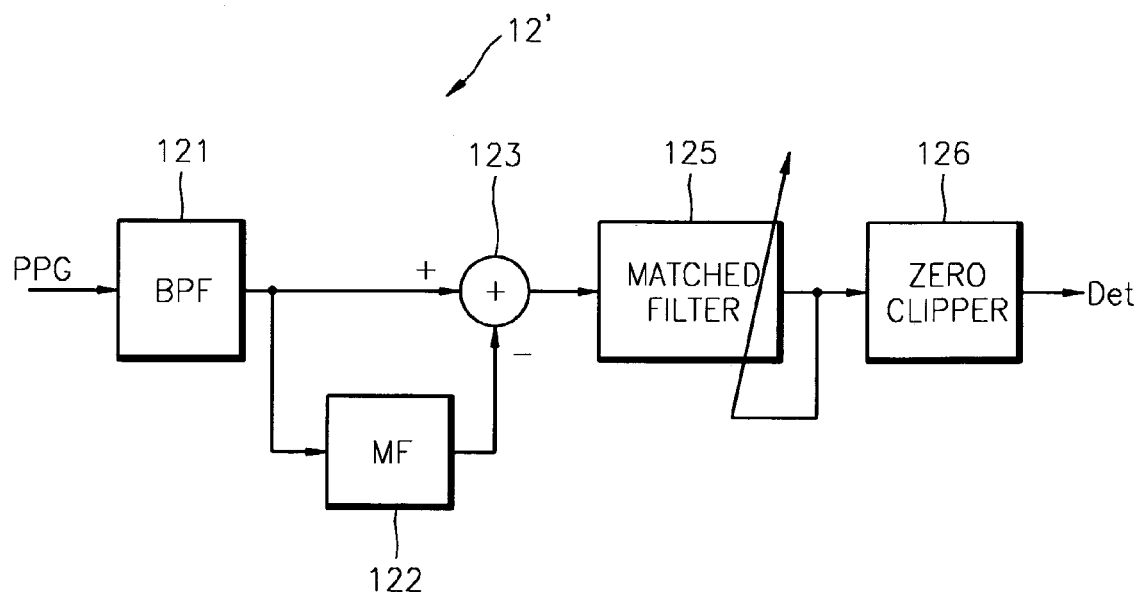

FIGS. 6A and 6B are graphs illustrating an example of ECG and PPG signals to be used in the analysis of a heart beat signal according to a preferred embodiment of the present invention, and FIGS. 7 and 8 are block diagrams illustrating in detail alternative constructions of the heart rate detector 12 of the emotion perceiving section 100 shown in FIG. 5, in which FIG. 7 shows the construction of the heart rate detector 12 in the case where an input signal is the ECG signal and FIG. 8 shows the construction of the heart rate detector 12' shown in the case where an input signal is the PPG signal.

Referring first to FIG. 7, the heart rate detector 12 includes a bandpass filter (BPF) 121, a median filter (MF) 122, an adder 123 and a Teager energy operator (TEO) section 124.

The BPF 121 is operative to pass only frequency components within a bandwidth covered by the ECG signal of input signals applied to the heart rate analyzer 11, and the MF 122 is operative to estimate a low-frequency noise component existing in the bandpass-filtered resultant signal. The adder 123 acts to calculate a difference between the bandpass-filtered resultant signal and the median-filtered resultant signal to eliminate a low-frequency noise component from the bandpass-filtered resultant signal. The signal output from the adder 123, whose low-frequency noise component has been removed, is supplied to the TEO section 124 to be used to extract the heart beat signal. Also, the TEO section 124 serves to detect the heart beat signal by applying a TEO function represented by $\Psi(x(t))$ to the signal output from the adder 123. Since the TEO generates a value proportional to the product of an instantaneous amplitude and an instantaneous frequency of the input signal, it is very useful for detection of a QRS peak in ECG. The details of this are disclosed in an article entitled "A New Interpretation of Nonlinear Energy Operator and Its Efficiency in Spike Detection", by S. Mukhopadhyay and G. C. Ray, contained in "IEEE TRANSACTIONS ON BIOMEDICAL ENGINEERING", Vol. 45, pp 180-187, 1998.

According to the heart rate detector 12 having the above-mentioned construction, the signal portions indicated by an arrow above the ECG signal shown in FIG. 6A are extracted as the heart beat signal Det.

Next, referring to FIG. 8, the heart rate detector 12' is shown to include a BPF 121, an MF 122, an adder 123, a matched filter 125 and a zero clipper 126.

The BPF 121 operates to pass only frequency components within a bandwidth covered by the PPG signal of input signals applied to the heart rate analyzer 11, and the MF 122 operates to estimate a low-frequency noise component existing in the bandpass-filtered resultant signal. The adder 123 acts to calculate a difference between the bandpass-filtered resultant signal and the median-filtered resultant signal to eliminate the low-frequency noise component from the bandpass-filtered resultant signal. The signal output from the adder 123, whose low-frequency noise component has been removed, is supplied to the matched filter 125 to be used to extract a specific signal (i.e. the heart beat signal) contained in the PPG signal.

The specific signal extracted by the matched filter 125 is supplied to the zero clipper 126 to be subjected to a zero clipping process to output the heart beat signal Det. Herein, the parameter of the matched filter 125 may be updated, if necessary. According to the heart rate detector 12' having the above-mentioned construction, the signal portions indicated by an arrow above the PPG signal shown in FIG. 6B are extracted as the heart beat signal Det.

Figure 9:
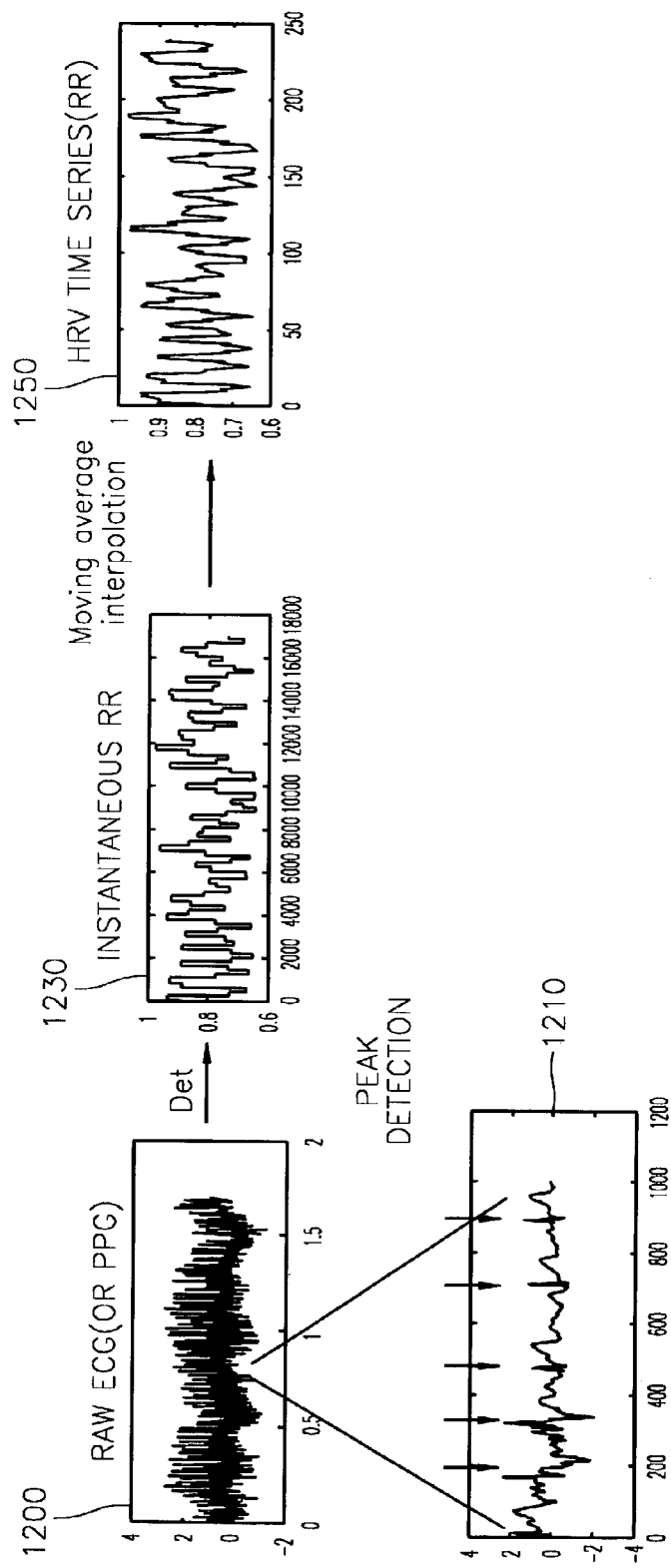
FIG. 9 is a graph illustrating a process of obtaining time series of heart rate variability (HRV) from a heart beat signal generated by the heart rate detector shown in FIGS. 7 and 8.

FIG. 9 is a graph illustrating a process of obtaining time series of HRV from a heart beat signal Det generated by the heart rate detectors 12 and 12' shown in FIGS. 7 and 8.

Referring to FIG. 9, in the case where a waveform 1200 of an ECG or PPG signal is acquired, an enlargement of its waveform shows the form of a waveform 1210. The ECG or PPG signal exhibits a periodic pulse like the waveform 1210, which represents a QRS waveform configured with a maximum value portion R, and minimum value portions Q and S positioned at both sides of the maximum value R.

In FIG. 9, the portions indicated by arrows above the waveform 1210 are an R waveform of a maximum value portion of the heart rate signal, and are extracted by the heart rate detector 12 or 12' shown in FIGS. 7 and 8 to exhibit an instantaneous R-R waveform 1230 of the ECG or PPG signal. Applying a moving average interpolation method to the instantaneous R-R waveform 1230 extracts time series of the HRV denoted by reference numeral 1250. The method of obtaining the time series 1250 of the HRV is disclosed in an article entitled "An Efficient Algorithm for Spectral of Heart Rate Variability" by R. D. Berger, et al., published in IEEE TRANSACTIONS ON BIOMEDICAL ENGINEERING, Vol. 33, 1986. Such an HRV signal becomes an index to quantitatively identify a degree of activation of a sympathetic nervous system and a parasympathetic nervous system.

Referring back to FIG. 5, the heart beat signal Det obtained by the heart rate detector 12 or 12' shown in FIGS. 7 and 8 is converted into time series of the HRV by the method shown in FIG. 9, and then is supplied to the spectrum analyzer 13 and the Mean/Std calculator 14.

The spectrum analyzer 13 estimates autoregressive (AR), moving average (MA), and autoregressive moving average (ARMA) models of various orders with respect to the time series of the HRV supplied from the heart rate detector 12, selects a special model of a specific order with a minimum index denoting an estimated error to choose an optimum time series model, and analyzes a spectrum of the HRV from the chosen optimum time series model by using a method of obtaining a spectrum. Herein, this method is called an ARMAsel algorithm. For this purpose, a method for estimating the index of the estimated error and each time series model is described in detail in an article entitled "Fact and Fictions in Spectral Analysis" by P. M. T. Broersen, found in IEEE TRANSACTIONS ON INSTRUMENTATION AND MEASUREMENT, Vol. 49, 2000.

Frequency domain parameters of HRV have been regarded as important factors in previous research, and have also been regarded as an important index in psychophysiological studies. The spectrum analyzer 13 according to the present invention employs the ARMAsel algorithm instead of a conventional periodogram method in which an extended signal ranging from a few minutes to 24 hours is a target for spectrum analysis so as to analyze a spectrum of HRV through observation of the time series signal for a short time period of 50 seconds or so. Then, the results of analysis by the spectrum analyzer 13 are supplied to the subtractor 20 as the feature values used to perceive an emotional state of a user.

In the meantime, the time series signal of HRV generated from the heart rate detector 12 or 12' is supplied to the Mean/

Std calculator 14 which, in turn, calculates a Mean and a Std with respect to a given time series, i.e., the detected heart beat signal.

Now, the detailed construction and operation of the SCR analyzer 15 included in the feature analyzer 10 shown in FIG. 5 will be described with reference to FIGS. 10 and 11.

Figure 10:
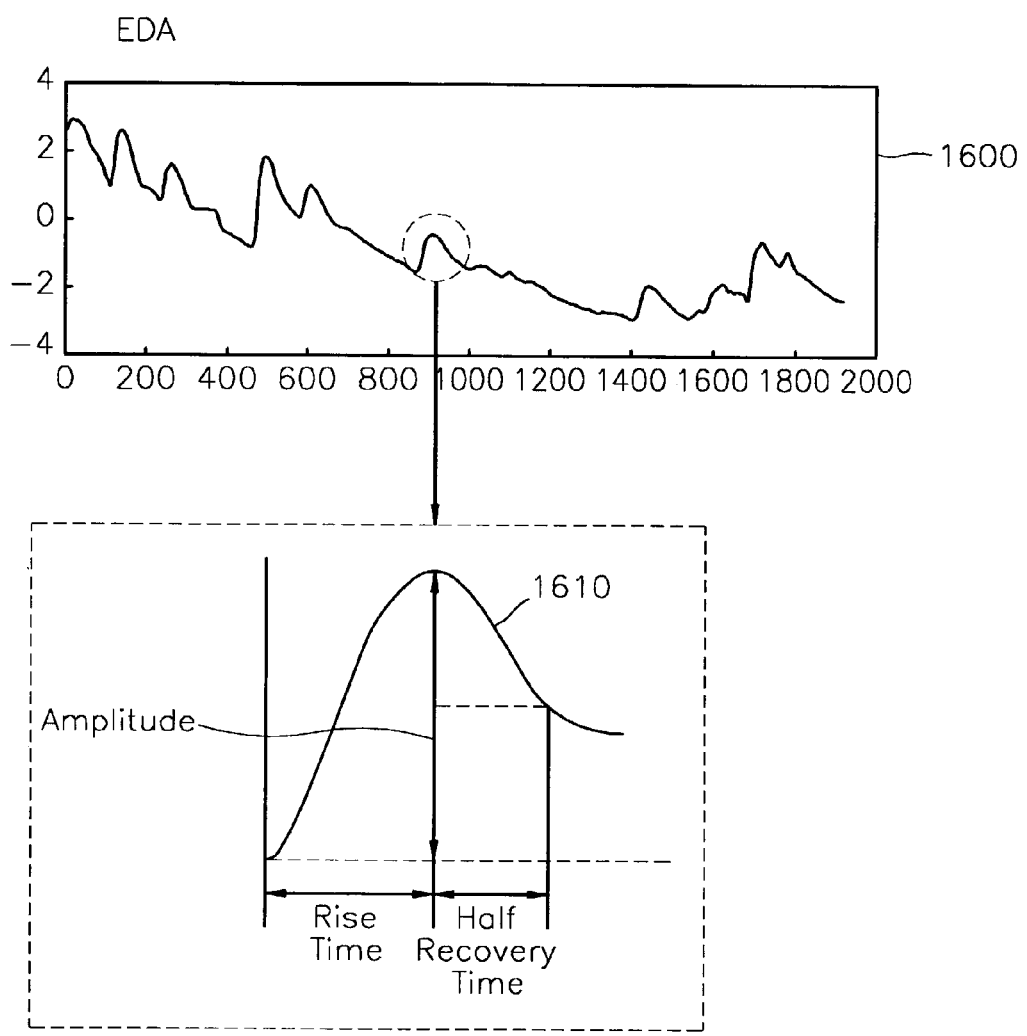
FIG. 10 is a graph illustrating the waveform of an electrodermal activity (EDA) signal used in the detection of skin conductance response (SCR) according to a preferred embodiment of the present invention.

FIG. 10 is a graphical view illustrating the waveform of an EDA signal used in the detection of SCR according to a preferred embodiment of the present invention.

Referring to FIG. 10, a waveform 1600 of the EDA signal and an enlarged waveform 1610 for a portion thereof with the characteristic of SCR to be extracted in the EDA signal waveform 1600 are similar to waveform 1210.

In FIG. 10, the EDA signal with the waveform denoted by reference numeral 1600 or 1610 is input to the SCR detector 16 included in the SCR analyzer 15.

Figure 11:
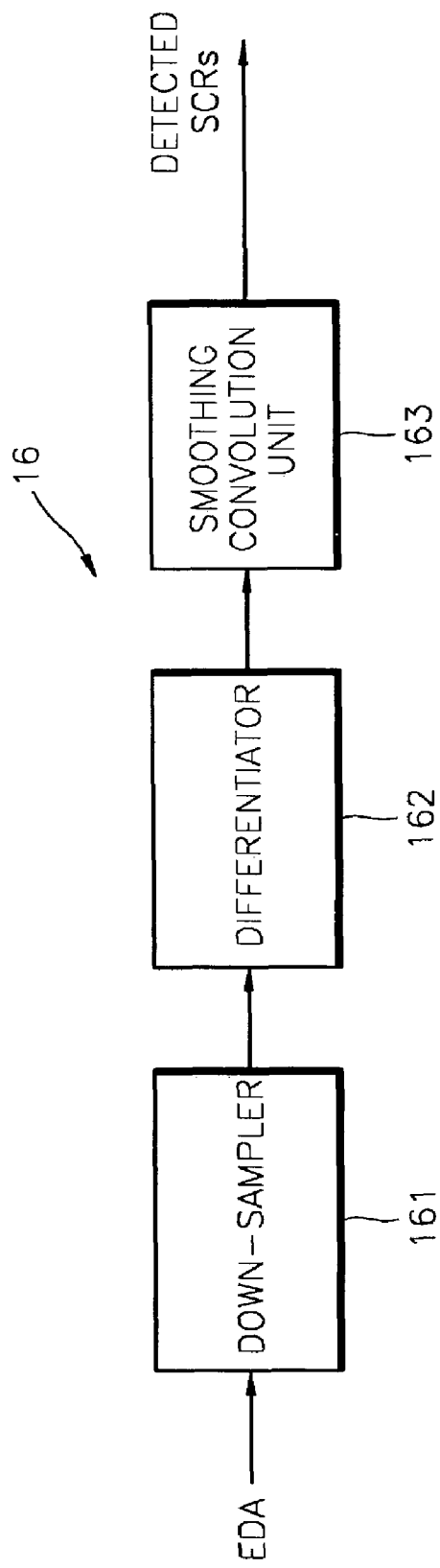
FIG. 11 is a block diagram illustrating the construction of an SCR detector of the emotion perceiving section shown in FIG. 5.

FIG. 11 is a block diagram illustrating the construction of the SCR detector 16 of the SCR analyzer 15 shown in FIG. 5.

Referring to FIG. 11, the SCR detector 16, which receives the EDA signal to detect SCR, includes a down-sampler 161, a differentiator 162, and a smoothing convolution unit 163.

The down-sampler 161 serves to down-sample the EDA signal input to the SCR detector 16 into 10 to 12 data or so. The differentiator 162 serves to differentiate the down-sampled result, and the smoothing convolution unit 163 acts to perform a smoothing convolution process with respect to the differentiated result by using a Bartlett window having a length of 20. The EDA signal input to the SCR detector 16 is output in the form of discrete SCR data.

The discrete SCR data generated from the SCR detector 16 is supplied to the SCR calculator 17 included in the SCR analyzer 15 which, in turn, generates feature values such as the generation number of SCR/time for a certain time period, the amplitude of SCR, the rise time of SCR, etc., for application to the subtractor 30.

The detailed construction and operation of the SKT Mean/Max calculator 18 included in the feature analyzer 10 shown in FIG. 5 will be described hereinafter with reference to FIGS. 12 and 13.

Figure 12:
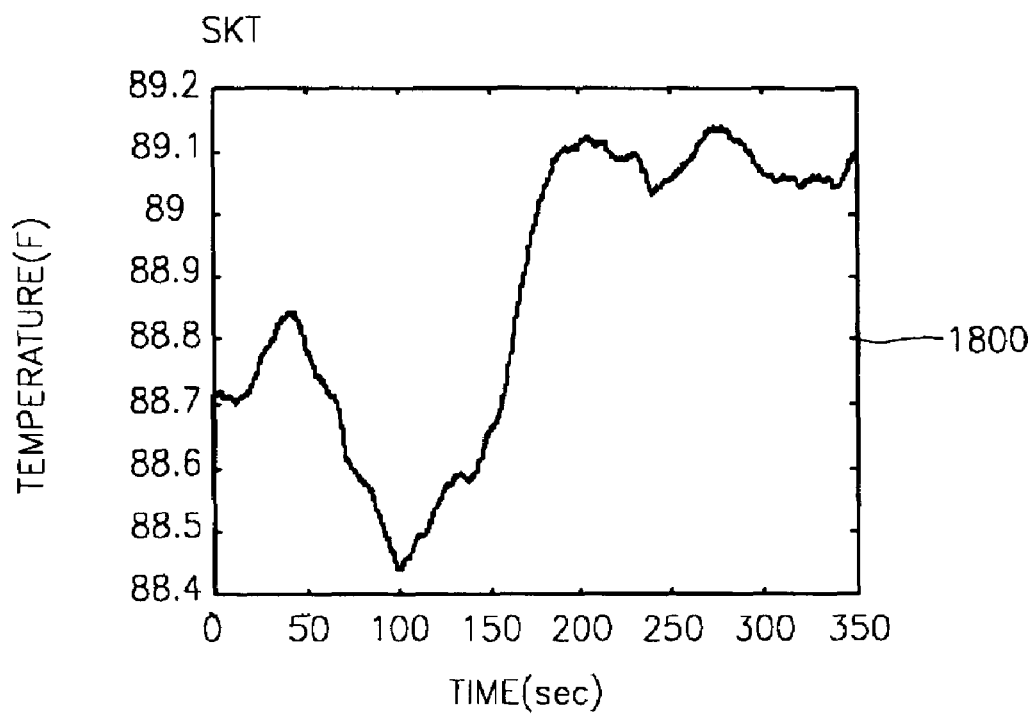
FIG. 12 is a graph illustrating the waveform of a skin temperature (SKT) signal used in the detection of variation in skin temperature.
Figure 13:
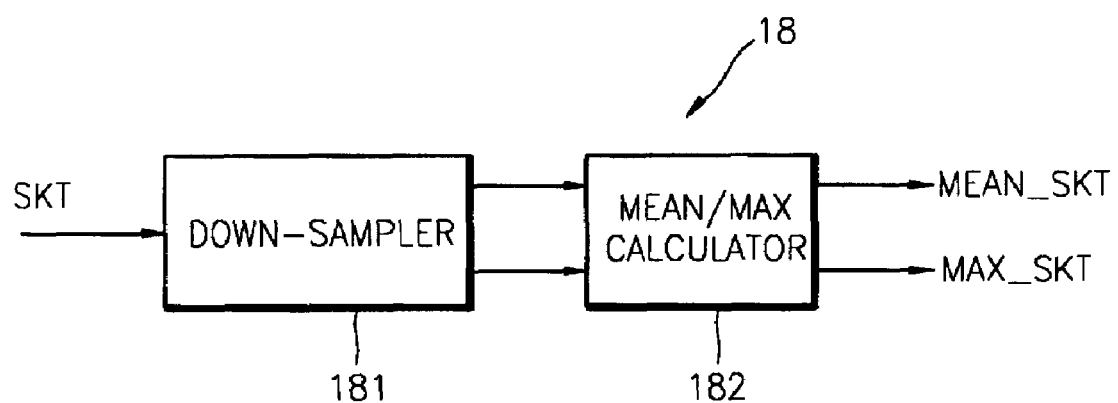
FIG. 13 is a block diagram illustrating the construction of an SKT Mean/Max calculator of the emotion perceiving section shown in FIG. 5.

FIG. 12 is a graph illustrating the waveform of an SKT signal used in the detection of variation in skin temperature, and FIG. 13 is a block diagram illustrating the construction of an SKT Mean/Max calculator 18 included in the feature analyzer 10 of the emotion perceiving section shown in FIG. 5.

Referring to FIG. 13, the SKT Mean/Max calculator 18 includes a down sampler 181 and a Mean/Max calculator 182.

The down sampler 181 functions to receive the SKT signal as shown in FIG. 12 and down-samples the received SKT signal into 100 data or so, and the Mean/Max calculator 182 functions to generate a mean value Mean_SKT and a maximum value Max_SKT of the down-sampled data as feature data values.

As mentioned above, once the heart rate analyzer 11, the SCR analyzer 15 and the SKT Mean/Max calculator 18 included in the feature analyzer 10 extract feature values needed to recognize the emotional state of a user from a plurality of physiological signals input to the emotion recognition unit 1 from the physiological signal acquiring unit 200 worn on the body of the user, the extracted feature values are sequentially applied to the subtractor 20 and the SVM unit 30 to recognize the emotional state of the user.

Figure 14:
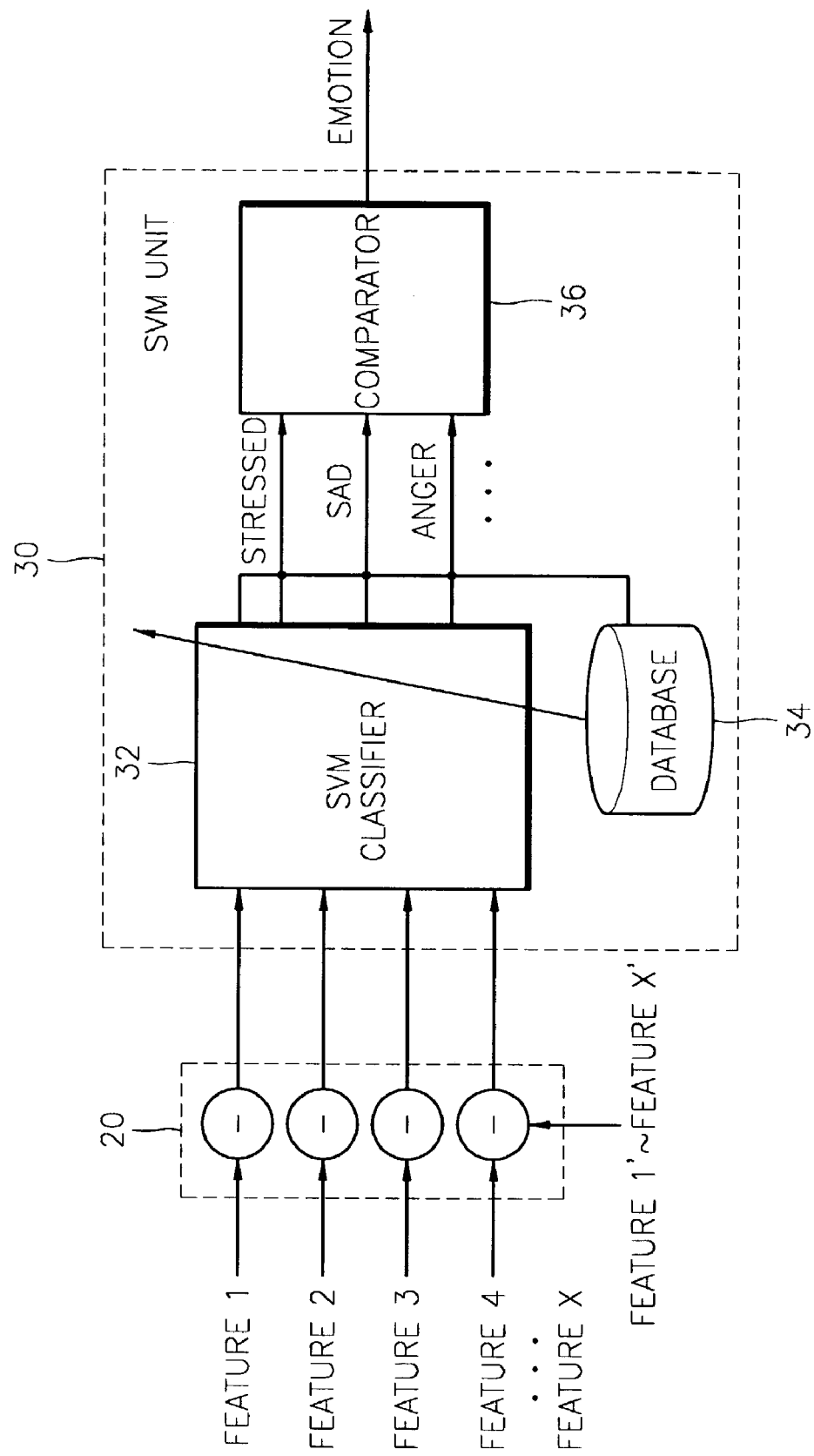
FIG. 14 is a block diagram illustrating the construction of a subtractor and SVM unit of the emotion perceiving section shown in FIG. 5.

FIG. 14 is a block diagram illustrating the construction of the subtractor 20 and SVM unit 30 of the emotion perceiving section shown in FIG. 5.

Referring to FIG. 14, the subtractor 20 stores feature values Feature 1'~Feature X' indicating an ordinary emotional state of the user as a standard for recognizing the current emotional state of the user.

The subtractor 20, acts to obtain differences between a plurality of feature values Feature 1~Feature X applied thereto from the heart rate analyzer 11, the SCR analyzer 15 and the SKT Mean/Max calculator 18 included in the feature analyzer 10, and a plurality of feature values Feature 1'~Feature X' representing an ordinary emotional state of the user to apply the obtained differences to the SVM unit 30.

The SVM unit 30 includes an SVM classifier 32 for training and classifying an emotional state of the user in response to the differences between the feature values of two groups output from the subtractor 20, a database 34 for storing the trained and classified results generated from the SVM classifier 32 therein, and a comparator 36 for comparing values of a plurality of emotional states classified by the SVM classifier 32 with each other to select a resultant emotional state of the user and output it.

At this time, the task of determining which predetermined emotional state of the user best corresponds to the extracted feature vectors amounts to a task of pattern recognition, and many kinds of classifiers may be applied for the purpose of the pattern recognition. Generally, once a feature vector indicating a specific emotional state forms one probability distribution in a multidimensional space and a probability density function corresponding to each emotional state is known, an optimum classifier may be implemented statistically by Bayes' law.

However, since it is actually impossible to correctly know such a probability density function, a parzen window classifier, a multiplayer perceptron, etc., which implicitly implement a rule corresponding to Bayes' rule, are mainly used. However, for such a conventional classifier, there has been a problem in that generalization characteristics are decreased, so errors frequently occur with respect to new data that is not used for training or learning. In addition, since the conventional pattern classifier has a considerably large dispersion of feature vectors and large overlapping portions between clusters corresponding to respective categories, there are many errors. Therefore, to address this problem, the present invention employs the SVM classifier 32 having an enhanced generalization characteristic as a pattern classifier for perceiving an emotional state of a user.

The SVM classifier 32 enables a high-dimensional and non-linear mapping to increase the chances of linear separation. Moreover, the SVM classifier 32 is constructed on the basis of an approach to implementing a linear separator with optimum generalization performance rooted in a statistical learning theory pioneered by Vapnik. The details of the SVM classifier with this characteristic are disclosed in "An Overview of Statistical Learning Theory" by V. N. Vapnik, IEEE TRANSACTIONS ON NEURAL NETWORKS, Vol. 10, 1999.

Figure 15A:
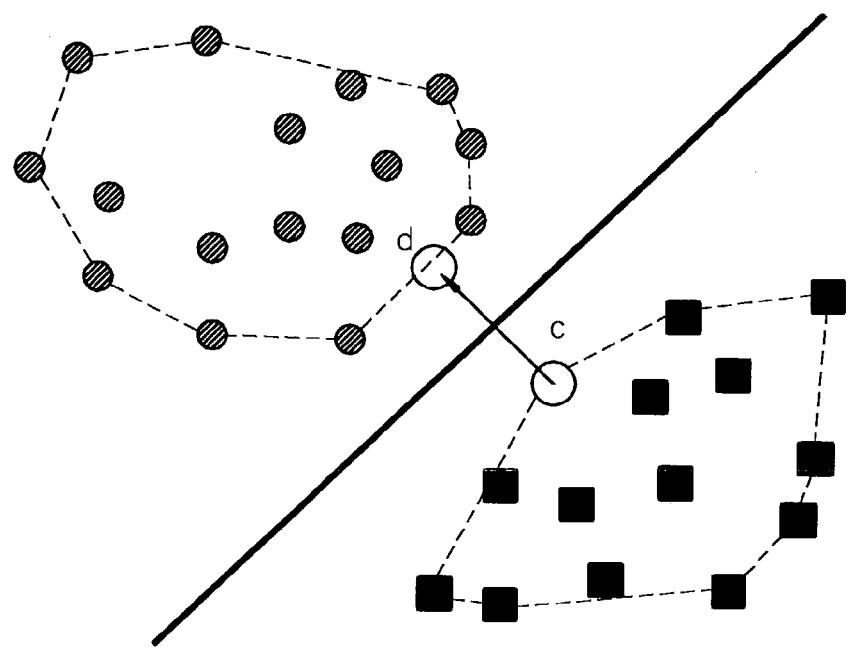
FIGS. 15A and 15B are views illustrating the results of classifying an emotion generated from an SVM classifier of the SVM unit shown in FIG. 14.
Figure 15B:
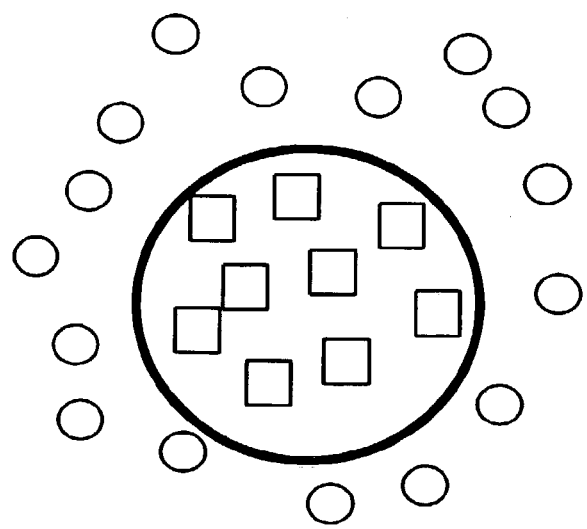

FIGS. 15A and 15B are views illustrating the results of classifying an emotion generated from an SVM classifier 32 of the SVM unit 35 shown in FIG. 14.

Referring to FIGS. 15A and 15B, the SVM classifier 32 according to the present invention proposes an optimum boundary (optimum separable surface) between feature data (i.e., user's emotions) by analyzing a high non-linear order in such a way that it is projected linearly in a feature space.

Referring back to FIG. 14, the results of classification of an emotion performed by the SVM classifier 32 include emotion categories. Once these results are available, they are output to the comparator 36 with different intensities for each emotion category represented numerically. For example, the intensity of each emotion is represented numerically such that an emotion corresponding to Stress is 0.3 (or 30%), an emotion corresponding to Sadness is 0.6 (or 60%), an emotion corresponding to Anger is 0.1 (10%), etc.

The comparator 36 of FIG. 14 receives a plurality of intensities with respect to a plurality of emotions from the SVM classifier 32 to perceive an emotion exhibiting the greatest intensity among the plurality of emotions as a resultant emotional state of the user to output the perceived result, i.e., Emotion. At this time, in the case where certain feature values are input to the SVM classifier 32, the database 34 stores information about which emotion is recognized with respect to the input feature values. A training of data for the database 31 is performed at the time of learning of the SVM classifier 32. Once the training of the SVM classifier 32 is completed, the data update for the database 31 is not performed. Accordingly, since the database 34 is an element necessary for a developer, it may not be provided to the emotion recognition system developed for end users.

Figure 16:
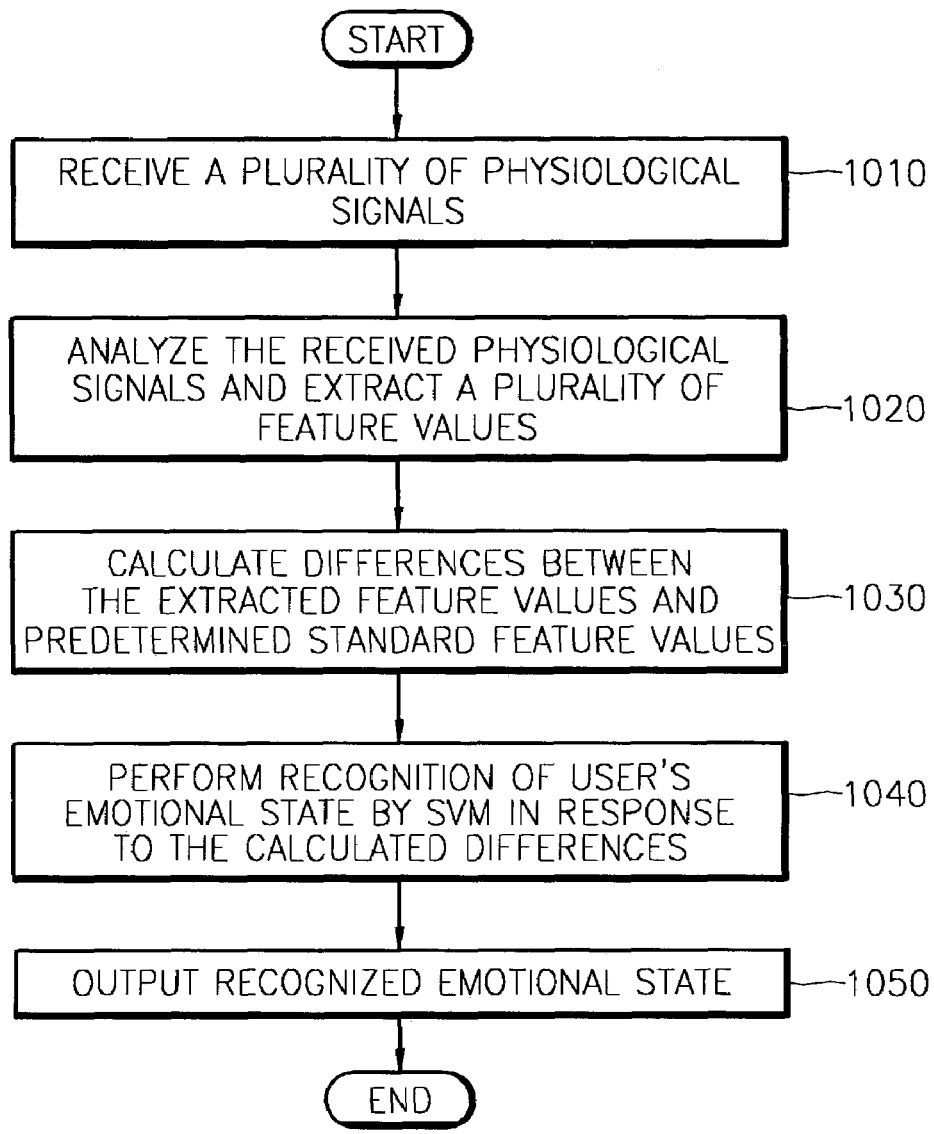
FIG. 16 is a flowchart illustrating a process for recognizing an emotion according to a preferred embodiment of the present invention.

FIG. 16 is a flowchart illustrating an emotion recognition method according to a preferred embodiment of the present invention.

Referring to FIG. 16, first, a plurality of physiological signals such as ECG/PPG, EDA and SKT are input to the physiological signal acquiring unit 200 of the emotion recognition system of the present invention from a user (step 1010). The physiological signals are acquired by the physiological signal acquiring unit 200 included in a sensor wearable on the body of the user, and are wirelessly transmitted to the emotion recognition unit 1.

The emotion recognition unit 1, which is configured with a certain processor having an emotion recognition program installed therein such as a computer, analyzes the plurality of physiological signals transmitted from the physiological signal acquiring unit 200 and extracts a plurality of feature values to be used for recognition of an emotional state of the user in response to the analyzed physiological signals (step 1020). The extracted plurality of feature values include, for example, a spectrum of a heart beat signal extracted from the ECG/PPG signal, an Mean and an Std of the heart beat signal, SCR related parameters detected from the EDA signal, and an Mean and an Max of the SKT signal, etc.

Subsequently, the extracted plurality of feature values are supplied to the subtractor 30. At this time, the subtractor 30 calculates differences between the extracted plurality of feature values and feature values used as a standard to perceive an emotional state of the user (step 1030). Herein, the feature values used as a standard to perceive an emotional state are ones indicating an ordinary emotional state of the user which does not lean toward a specific emotion, and are previously stored in the subtractor 20.

In this way, when the difference values are obtained, they are supplied to the SVM unit 30 which, in turn, performs recognition of an emotional state of the user. The SVM unit 30 classifies an emotional state of the user into a plurality of emotional types in response to the obtained differences, and selects an emotion exhibiting the greatest intensity among the classified emotional types as a resultant emotional state of the user to output the selected emotion (step 1050).

Figure 17:
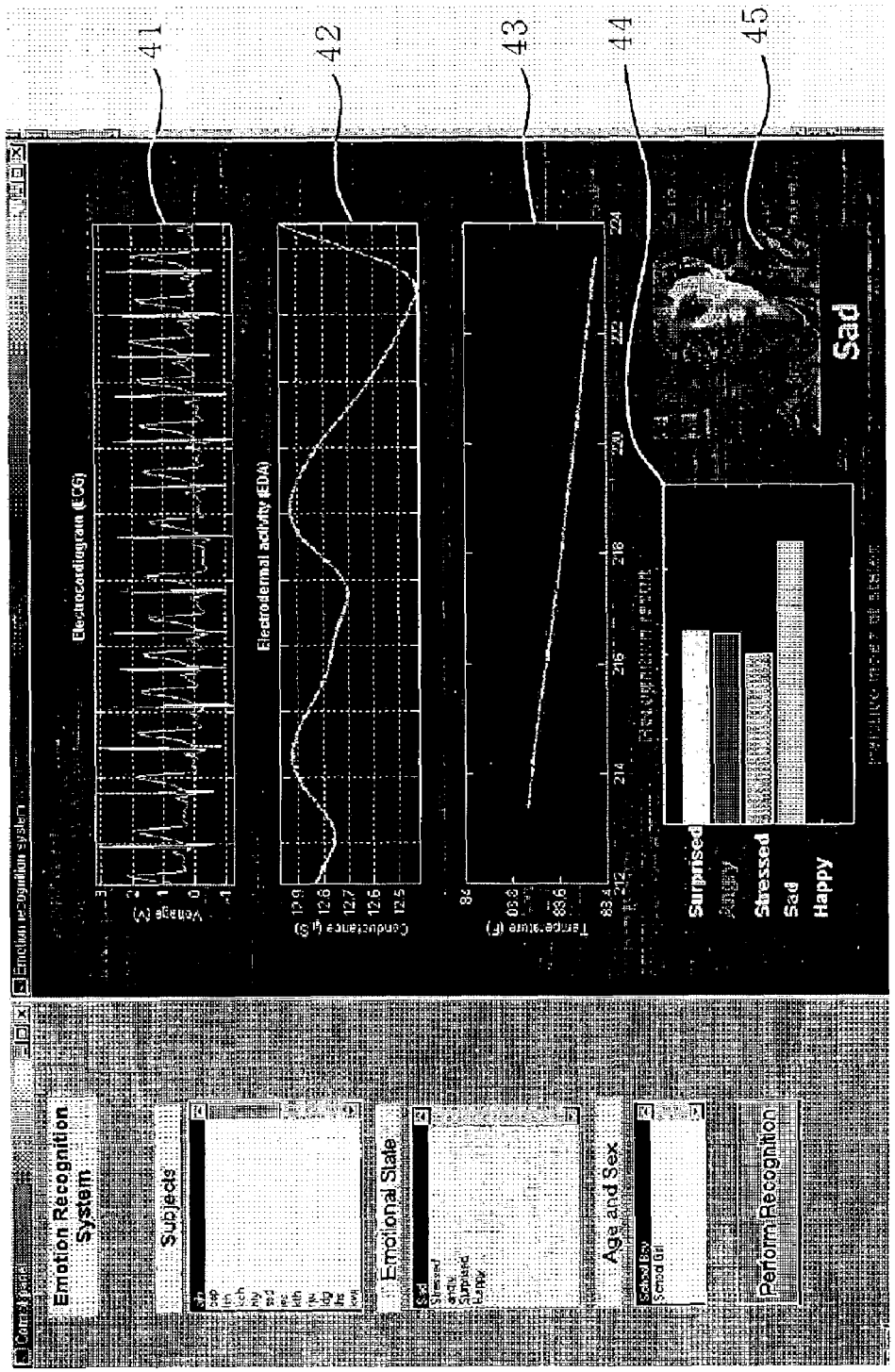
FIG. 17 is a view illustrating the results of performing an emotion recognition method according to a preferred embodiment of the present invention.

FIG. 17 is a view illustrating the results of performing an emotion recognition method according to a preferred embodiment of the present invention.

Referring to FIG. 17, the emotion recognition system according to the present invention receives physiological signals of the user indicated by reference numerals 41 to 43 and displays the result of classifying an emotion on a given screen window in the form of an appropriate facial expression indicated by reference numeral 44. Also, an emotion (for example, "Sad") with the highest percentage among the results of classifying an emotion is output as the resultant perceived emotional state of the user as indicated by reference numeral 45.

The emotion recognition system and method according to the present invention have the following advantages over conventional methods. For example, conventional emotion recognition methods employ electroencephalogram (EEG), electromyogram (EMG) for facial muscles, etc., so that a plurality of electrodes are attached on the skin of head or the skin of face which makes it possible to hurt a person's feeling and cause inconvenience. On the other hand, the emotion recognition method of the present invention employs physiological signals non-invasively acquired through a sensor wearable in the form of a wrist watch on the body, which makes it very easy and practical to use. Moreover, the emotion recognition system and method according to the present invention have a remarkably high emotion recognition rate compared to conventional methods through only an observation of physiological signals for a short time period of 50 seconds or so.

Also, the present invention may be implemented with a program code installed on any type of recording medium readable by a computer. Examples of a recording medium readable by a computer include a read only memory (ROM), a random access memory (RAM), a compact disk-ROM (CD-ROM), a magnetic tape, a floppy disk, an optical data storage medium, etc., and may include a medium embodied in the form of carrier waves (for example, transmission through the Internet). Further, the recording medium readable by a computer may be distributed among computer systems connected to a network so that it can be stored and executed in the form of a program code readable by the connected computers.

As described above, according to the emotion recognition system and method of the present invention, a user acquires physiological signals from a sensor that can be worn continuously on his or her body without discomfort, and monitors the acquired physiological signals for a short time period to correctly perceive his or her own emotional state.

While this invention has been particularly shown and described with reference to preferred embodiments thereof, it will be understood by those skilled in the art that various changes in form and details may be made therein without departing from the spirit and scope of the invention as defined by the appended claims.

What is claimed is:

1. An emotion recognition system, comprising:
a physiological signal acquiring unit wearable by a user in the form of a wrist watch, acquires one or more physiological signals from a user
and wirelessly transmit the acquired physiological signals
and an emotion recognition unit receives the physiological signals transmitted from the physiological signal acquiring unit and monitor them for a time period to perceive an emotional state of the user,
wherein the emotion recognition unit comprises:
a feature analyzer analyzes features of the physiological signals and generate feature values corresponding to the results of the analysis;
a subtractor obtains differences between the feature values of the results generated by the feature analyzer and feature values used as a standard to perceive an emotional state of the user; and
an emotion classifier analyzes the differences obtained by the subtractor to classify an emotion into a plurality of emotional categories to perceive an emotional category exhibiting the greatest intensity to be an emotional state of the user.

2. The emotion recognition system as claimed in claim 1, wherein the physiological signal acquiring unit comprises:
- one or more sensors adapted to non-invasively sense one or more physiological signals of the user;
- an amplifier-filter adapted to amplify and filter the one or more physiological signals applied thereto from the one or more sensors and output the one or more amplified and filtered signals;
- a multiplexer adapted to classify the amplified and filtered signals applied thereto from the amplifier-filter with respect to each physiological signal and output the classified physiological signals in the form of analog signals;
- an A/D converter adapted to convert the classified analog physiological signals applied thereto from the mulitplexer into the form of digital signals and output the converted digital signals; and
- an RF transmitter adapted to wirelessly transmit the converted digital signals applied thereto from the A/D converter to the emotion recognition unit in the form of RF signals.

3. The emotion recognition system as claimed in claim 1, wherein the emotion recognition unit is an arithmetic and logical unit (ALU) having an algorithm stored therein for analyzing the physiological signals of the user transmitted from the physiological signal acquiring unit and recognizing the user's emotional state.

4. The emotion recognition system as claimed in claim 1, wherein the feature analyzer comprises:
- a heart rate analyzer adapted to receive either one of an EGG signal and a PPG signal to detect a heart beat signal and extract the feature values associated with the detected heart beat signal;
- a skin conductance response (SCR) analyzer adapted to receive an EDA signal to extract the feature values associated with an SCR; and
- an skin temperature (SKT) analyzer adapted to receive an SKT signal to extract feature values associated with SKT.

5. The emotion recognition system as claimed in claim 4, wherein the heart rate analyzer comprises:
- a heart rate detector adapted to receive any one of the ECG and PPG signals to detect a heart beat signal and adapted to convert the detected heart beat signal into time series of heart rate variability HRV;
- a spectrum analyzer adapted to analyze a spectrum of the heart beat signal in response to the time series of HRV; and
- a mean/standard deviation calculator adapted to calculate a mean value and a standard deviation value of the detected heart beat signal in response to the time series of HRV.

6. The emotion recognition system as claimed in claim 5, wherein the heart rate detector comprises:
- a bandpass filter adapted to pass only frequency components within the same frequency band as the ECG signal of input signals applied to the heart rate analyzer;
- a median filter (MF) adapted to estimate a low-frequency noise component existing in the bandpass-filtered resultant signal;
- an adder adapted to add an inverse number of the median-filtered resultant signal to the bandpass-filtered resultant signal to eliminate the low-frequency noise component from the bandpass-filtered resultant signal; and
- a Teager energy operator (TEO) section adapted to detect the heart beat signal by applying a TEO to an output signal from the adder.

7. The emotion recognition system as claimed in claim 5, wherein the heart rate detector comprises:
- a bandpass filter adapted to pass only frequency components within the same frequency band as the PPG signal of input signals applied to the heart rate analyzer;
- an MF adapted to estimate a low-frequency noise component existing in the band pass-filtered resultant signal;
- an adder adapted to add an inverse number of the median-filtered resultant signal to the bandpass-filtered resultant signal to eliminate the low-frequency noise component from the bandpass-filtered resultant signal;
- a matched filter adapted to extract the heart beat signal from a signal output from the adder; and
- a zero clipper adapted to perform a zero clipping process with respect to the extracted heart beat signal from the matched filter.

8. The emotion recognition system as claimed in claim 1, wherein the subtractor uses feature values representing an ordinary emotional state of the user as a standard to perceive the emotional state of the user.

9. The emotion recognition system as claimed in claim 1, wherein the emotion classifier comprises:
- a support vector machine (SVM) classifier adapted to analyze the differences obtained by the subtractor and classify an emotion of the user into a plurality of emotional categories to output the result of classifying the emotion in the form of a plurality of intensities each corresponding to an associated one of a plurality of emotions; and
- a comparator adapted to compare the plurality of intensities with respect to the plurality of emotions classified by the SVM classifier with each other so as to perceive an emotion exhibiting the greatest intensity among the classified emotions to be a resultant emotional state of the user and output it.

10. The emotion recognition system as claimed in claim 9, wherein the emotion classifier further comprises a database adapted to store a plurality of emotional data used to train the SVM classifier and the trained result of the SVM classifier according to the plurality of emotional data.

11. An emotion recognition method, comprising the acts of:
- receiving one or more physiological signals from a user wherein the physiological signals are acquired non-invasively;
- analyzing the received physiological signals and extracting a plurality of feature values to be used for recognition of an emotional state of the user in response to the result of analyzing the received physiological signals;
- calculating differences between the extracted plurality of feature values and predetermined feature values used as a standard to perceive an emotional state of the user;
- classifying an emotional state of the user into a plurality of emotional categories in response to the calculated differences; and
- selecting an emotion exhibiting the greatest intensity among the classified emotional categories as a resultant emotional state of the user and outputting the selected emotion.

12. The emotion recognition method as claimed in claim 11, wherein the physiological signals comprise PPG, EGG, EDA and SKT signals which are acquired non-invasively.

13. The emotion recognition method as claimed in claim 11, wherein the feature values used as a standard to perceive the emotional state of the user are feature values representing an ordinary emotional state of the user.

14. The emotion recognition method as claimed in claim 11, wherein the classifying step uses an SVM classifier for classifying the emotional state of the user into the plurality of emotional categories based on a statistical learning theory.

* * * * *